(12) United States Patent
Tufts et al.

(10) Patent No.: US 7,862,763 B2
(45) Date of Patent: Jan. 4, 2011

(54) METHODS OF QUALITY CONTROL IN CONCRETE BLOCK PRODUCTION

(75) Inventors: Paul Randal Tufts, Eagan, MN (US);
Jimmie L. Mugge, Eagan, MN (US);
Paul Joseph Johnson, Clearwater, MN (US)

(73) Assignee: Anchor Wall Systems, Inc., Minnetonka, MN (US)

( * ) Notice: Subject to any disclaimer, the term of this patent is extended or adjusted under 35 U.S.C. 154(b) by 1149 days.

(21) Appl. No.: 11/159,489

(22) Filed: Jun. 23, 2005

(65) Prior Publication Data

US 2006/0290020 A1    Dec. 28, 2006

(51) Int. Cl.
*B28B 3/00* (2006.01)
(52) U.S. Cl. .................. 264/333; 264/219; 264/163
(58) Field of Classification Search ................ 264/333, 264/219, 163; 428/141
See application file for complete search history.

(56) References Cited

U.S. PATENT DOCUMENTS

| | | | |
|---|---|---|---|
| 1,086,975 A | 2/1914 | Aaronson | |
| 3,981,953 A | 9/1976 | Haines | |
| 5,183,616 A | 2/1993 | Hedrick | |
| 6,063,444 A | 5/2000 | Dax | |
| 2003/0126821 A1 | 7/2003 | Scherer et al. | |

FOREIGN PATENT DOCUMENTS

| | | |
|---|---|---|
| EP | 0 657 260 | 12/1994 |
| EP | 0 657 260 A1 | 6/1995 |
| JP | 04 155208 A | 5/1992 |
| JP | 5-86684 | 4/1993 |

OTHER PUBLICATIONS

International Search Report and Written Opinion for PCT/US2006/023432.

*Primary Examiner*—Christina Johnson
*Assistant Examiner*—Larry Thrower
(74) *Attorney, Agent, or Firm*—Merchant & Gould P.C.

(57) ABSTRACT

The invention relates to a method of controlling the quality of blocks that are produced front face-up in a mold, and verifying the accuracy of the production of such blocks, to ensure that the blocks are manufactured with consistent quality and minimal block-to-block variability. Measurement locations are formed on the front faces of predetermined blocks. By measuring the distances between the measurement locations and the rear faces and comparing with a target distance, any variation provides an indication that the blocks are not being properly formed. The process variables, such as the alignment of the compression head and/or the pressure plates to the mold, can then be adjusted accordingly.

11 Claims, 8 Drawing Sheets

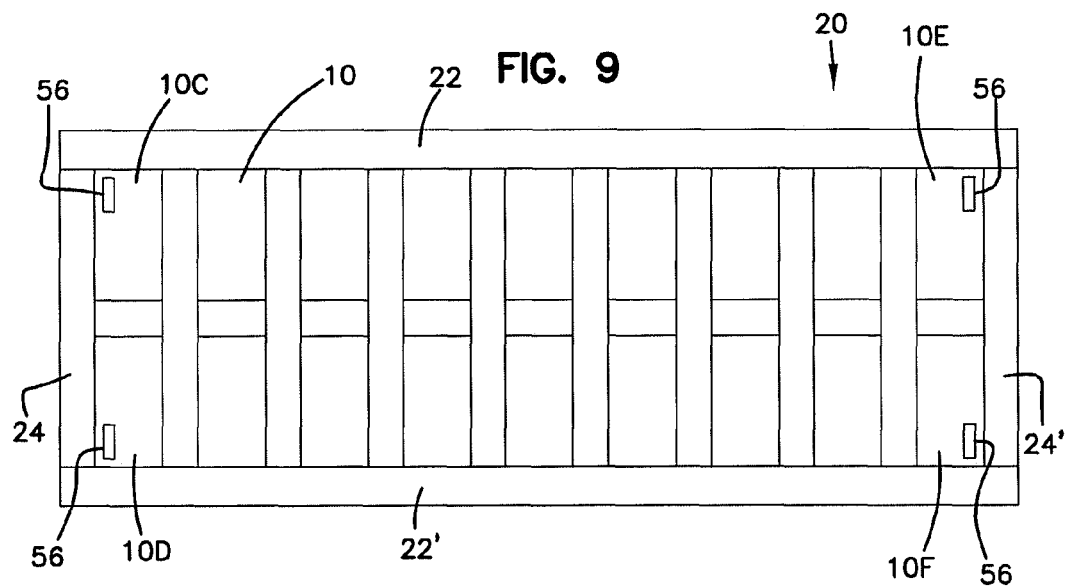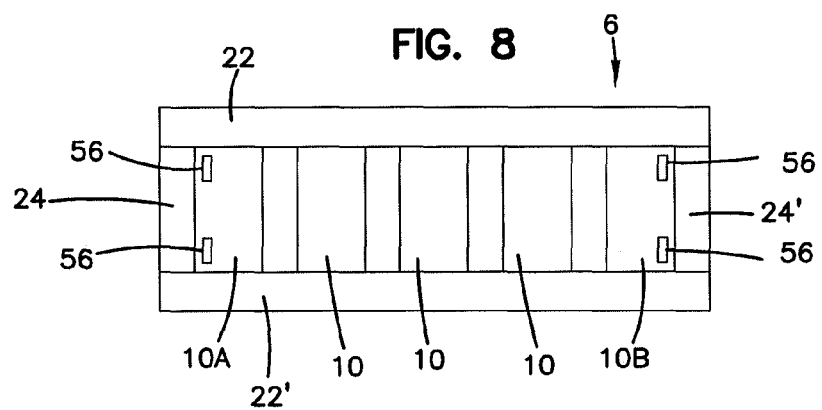

METHODS OF QUALITY CONTROL IN CONCRETE BLOCK PRODUCTION

FIELD OF THE INVENTION

The invention relates generally to the manufacture of concrete blocks. More specifically, the invention relates to the manufacture of concrete blocks suitable for use in landscaping applications, such as retaining walls, and methods of quality control relating to the production of such blocks.

BACKGROUND OF THE INVENTION

Modem, high speed, automated concrete block plants typically make use of molds that are configured to produce multiple blocks simultaneously. These molds contain multiple mold cavities, where each cavity is typically open at the top and at the bottom. The molds are mounted in machines which cyclically station a pallet below the mold to close the bottom of the mold cavities, deliver dry cast concrete into the mold cavities through the open top of the mold cavities, densify and compact the concrete by a combination of vibration and pressure, and strip the mold by a relative vertical movement of the mold and the pallet.

There is a demand for a concrete block that, when laid up into a wall or other structure with other blocks, has an exposed face that has a natural appearance so that a resulting wall constructed from a plurality of the blocks appears to have been constructed with naturally-occurring, rather than man-made, materials.

Known methods for producing block faces with a natural appearance is by the splitting process described in U.S. Pat. No. 5,827,015, or by the splitting process described in U.S. Pat. No. 6,321,740.

Another method for achieving a block face that has a more natural appearance than is achievable by known splitting processes is disclosed in U.S. Patent Application Publication No. 2003/0126821. As disclosed in Publication No. 2003/0126821, a mold is provided that has a plurality of block cavities arranged in a row, with each cavity being configured to produce a concrete block with the block oriented with its front face facing upward in the cavity. Pressure plates, also known as a "stripper shoes," are connected to a compression head. The pressure plates, which have a predetermined three-dimensional pattern formed therein, are pressed into dry cast concrete within the mold cavities by the compression head to densify the concrete and impart the patterns to the front faces of the blocks being formed in the cavities.

When imparting three-dimensional patterns to the faces of the blocks using pressure plates, as in Publication No. 2003/0126821, it is important that the compression head and the pressure plates connected thereto apply sufficient compaction pressure on the concrete in order to adequately densify the concrete. Insufficient densification of the concrete can result in a block that does not have the expected and desired strength properties. In addition, it is important that the compression head and pressure plates be level so they come down straight and contact the dry cast concrete in the mold cavities with even pressure across all of the cavities. If the head and the pressure plates are not level, uneven pressures may be exerted on the concrete in the cavities, thereby resulting in insufficient or uneven densification of the concrete in one or more of the cavities. Uneven densification can result in a block having strength properties that vary greatly across the block.

Further, insufficient and uneven densification can result in block-to-block variations in the dimensions of the blocks, particularly the depth of the block between the front and rear face of each block. Variability in the depths of the blocks can cause a wall or other structure built with the blocks to appear to be poorly constructed and to be visually unattractive.

There is a need for controlling the quality of blocks that are produced front face-up in a mold, to ensure that the blocks are manufactured with consistent quality and minimal block-to-block variability.

SUMMARY OF THE INVENTION

The invention relates to a method for producing concrete blocks front face-up in a mold and that have a three-dimensional pattern imparted to them by pressure plates. The invention also relates to a method of controlling the quality of blocks that are produced front face-up in a mold, and verifying the accuracy of the production of such blocks, to ensure that the blocks are manufactured with consistent quality and minimal block-to-block variability.

The blocks are formed front face-up in a mold having at least one row of block-forming cavities, and a three-dimensional pattern is imparted to the front face of each block by patterned pressure plates connected to a compression head. Predetermined ones of the pressure plates, for example the pressure plates associated with each end cavity, are configured to produce measurement locations on the front faces of the blocks. By measuring the distances between the measurements locations and the rear faces of the blocks, any variations between the measured distances and the target distances indicates that the compression head and the pressure plates connected thereto did not adequately compress the concrete in the mold cavity, or are not oriented properly and need to be adjusted.

BRIEF DESCRIPTION OF THE DRAWINGS

FIG. 8 is a top view of the concrete blocks formed in the mold of FIG. 2 with a preferred arrangement of measurement locations.

FIG. 9 is a top view of the concrete blocks formed in the mold of FIG. 3 with a preferred arrangement of measurement locations.

DETAILED DESCRIPTION OF THE PREFERRED EMBODIMENT

The present invention provides a method for producing concrete blocks front face-up in a mold and that have a three-dimensional pattern imparted to the front faces by pressure plates. The invention also relates to a method of controlling the quality of blocks that are produced front face-up in a mold, and verifying the accuracy of the production of such blocks, to ensure that the blocks are manufactured with consistent quality and minimal block-to-block variability.

Measurement locations are formed on the front faces of the blocks. Preferably, the measurement locations are formed on the front faces of the blocks located at the ends or corners of the mold. Measurement locations at the ends or corners of the mold will tend to have greater sensitivity to production variability. However, the measurement locations may be formed on the front faces of any of the blocks in the mold, and the measurement locations may be formed at any position on the front faces of the blocks. Preferably, to facilitate the measurement of the blocks in a production process, each measurement location defines the same distance between it and the rear face of the respective block when the blocks are correctly formed. However, because the front face of a block is not necessarily parallel to the back face of a block, and because the measurement locations may be formed at any position on the front face of a block, the measurement locations may not necessarily define the same distance between it and the rear face of the respective block. In either case, if the measured distance from each measurement location to the rear face of the block equals the target distance, one knows that the block has been properly formed with the expected densification of the concrete. On the other hand, if the measured distance does not equal the target distance, that provides an indication that the concrete may not have been adequately densified and that the block may not have been properly formed.

Further, if the measured distance on a block formed at one position of the mold does not equal the target distance, but the measured distance on a block formed at another position of the mold does equal the target distance, one knows that the blocks have not been properly and consistently formed within each of the cavities in the mold.

If the comparison between the measured distances and the target distances indicate that blocks have not been properly formed, corrective action may be taken. Variables that may be corrected include the alignment of the stripper shoe, the amount of concrete inserted into each mold cavity, the amount of force exerted by the stripper shoe, the density of the concrete mixture, or the composition of the concrete mixture. The corrective action may also include the replacement of worn components.

Figure 1:
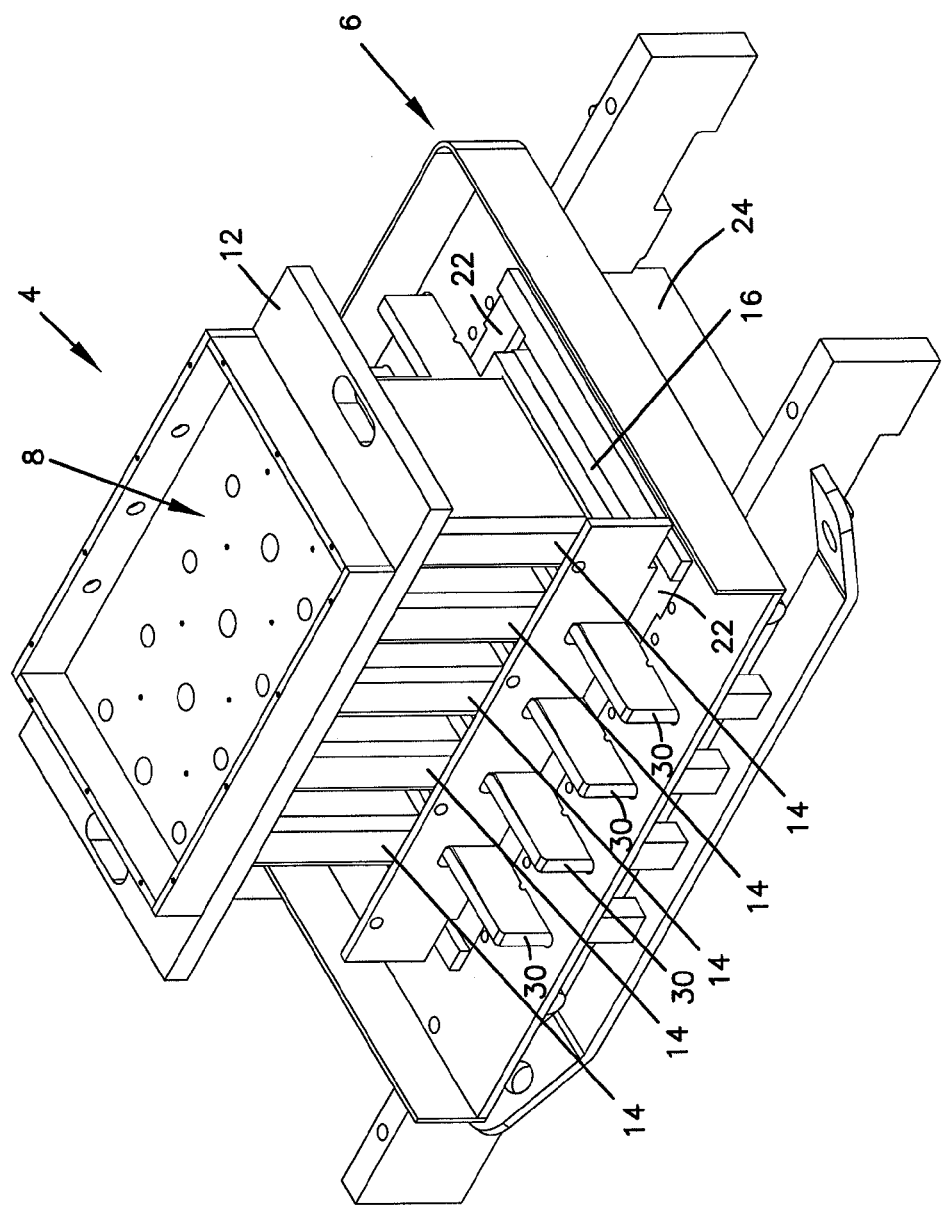
FIG. 1 is a perspective view of a concrete block mold.

FIG. 1 illustrates a mold assembly 4 comprising a mold 6 and a compression head assembly 8. The mold 6 comprises a row of block-forming cavities 10 that are visible in FIG. 2. In the embodiment illustrated in FIGS. 1 and 2, there are five block-forming cavities 10. The mold 6 comprises a generally rectangular structure formed by a pair of side walls 22, 22' and a pair of end walls 24, 24'. Division plates 30 subdivide the mold 6 into the block-forming cavities 10.

Figure 3:
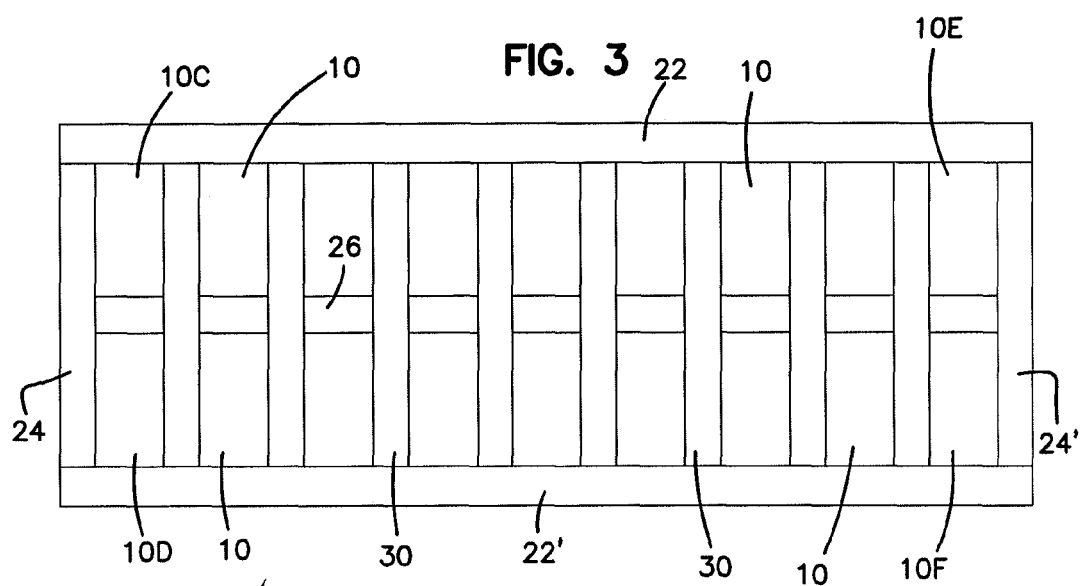
FIG. 3 is a top view of another embodiment of a concrete block mold with two rows of block-forming cavities.

Another example of an arrangement of mold cavities in a mold 20 is illustrated in FIG. 3. The mold 20 includes two rows of block-forming cavities 10 disposed side-by-side and separated by a dividing wall 26. In the illustrated embodiment, each row of the mold 20 includes nine block-forming cavities 10.

Returning to FIG. 1, the head assembly 8 includes a compression head 12 in the form of a plate. The head 12 is actuated by an actuating mechanism in a manner known in the art so that the head 12 is moveable vertically up and down to bring about compaction of dry cast concrete that is deposited into the cavities 10 and to assist in stripping the pre-cured blocks from the block-forming cavities 10.

Connected to and extending from the bottom of the head 12 are a plurality of stand-offs 14, one stand-off for each block-forming cavity 10. The stand-offs 14 are spaced from each other, with the longitudinal axis of each stand-off oriented perpendicular to the plane of the head 12 and extending generally centrally through the respective block-forming cavity 10.

A pressure plate 16, also called a stripper shoe, is connected to the end of each stand-off 14. The stripper shoe 16 is rectangular in shape and is dimensioned so that it may enter the respective cavity 10 through the top of the cavity to contact the concrete to compact the concrete, and to travel through the cavity during discharge of the pre-cured block. Each stripper shoe 16 also has a face that comprises a three-dimensional pattern 18. When the stripper shoe 16 is pressed into the concrete in the mold cavity, the three-dimensional pattern is imparted to the concrete in the cavity. Further details on using a stripper shoe to compact concrete and impart a three-dimensional pattern to the front face of a block, and for creating a suitable three-dimensional pattern on the stripper shoe, are disclosed in U.S. Patent Application Publication No. 2003/0126821 which is incorporated herein by reference in its entirety.

Figure 4:
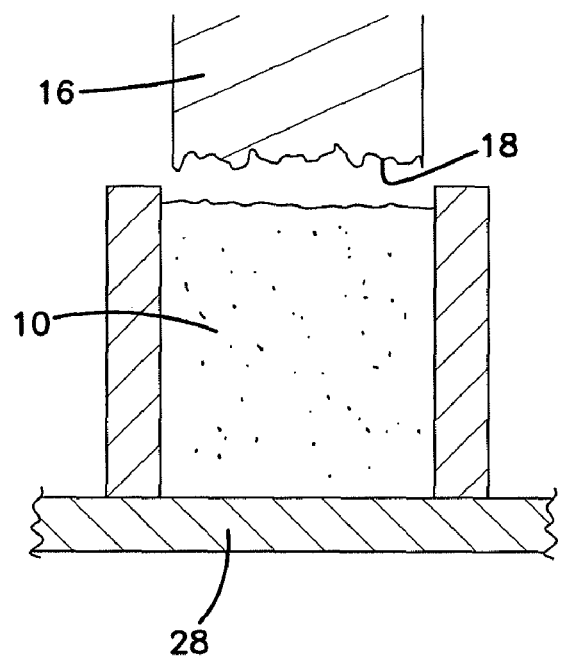
FIG. 4 is a cross-sectional view of one of the block-forming cavities and a patterned pressure plate that imparts a three-dimensional pattern to the front face of a concrete block.

Turning now to FIG. 4, each cavity 10 is configured to form a block where the front face of the block faces upward toward the open top of the mold cavity, and the rear face of the block rests on a pallet 28 that is positioned underneath the mold cavities to temporarily close the open bottoms of the mold cavities. The top, bottom and side faces of the blocks are formed by the side walls, end walls and division plates of the mold. Further details on a suitable mold cavity for forming a block face-up in the cavity are disclosed in U.S. Patent Application Publication No. 2003/0126821.

After dry cast concrete is deposited into the mold cavity 10, the stripper shoe 16 is brought down through the open top of the cavity 10 to contact the concrete to compact the concrete and densify it. The amount of densification of the concrete is selected so that the finished blocks will have the desired weight, density, and performance characteristics. During compaction, the three-dimensional pattern is imparted to the front face of the block.

The general process of forming the blocks is disclosed in U.S. Patent Application Publication No. 2003/0126821. Generally, the process is initiated by mixing the dry cast concrete that will form the blocks. Dry cast, no slump concrete is well known in the art. Once the concrete is mixed, it is transported to a hopper, which holds the concrete near the mold. When it is desired to form blocks, the pallet 28 is positioned beneath the mold so as to close the bottoms of the cavities 10. The appropriate amount of dry cast concrete from the hopper is then loaded, via one or more feed drawers, into the block-forming cavities 10 through the open tops of the cavities 10. The process and equipment for transporting dry cast concrete and loading a block-forming cavity are well known in the art.

The dry cast concrete in the cavities 10 must next be compacted to densify it. This is accomplished primarily through vibration of the dry cast concrete, in combination with the application of pressure exerted on the mass of dry cast concrete from above. The vibration can be exerted by vibration of the pallet underlying the mold (table vibration), or by vibration of the mold box (mold vibration), or by a combination of both actions. The pressure is exerted through the compression head 12 that is connected to the patterned stripper shoes 16 that contact the mass of dry cast concrete from above. The timing and sequencing of the vibration and compression is variable, and depends upon the characteristics of the dry cast concrete used and the desired results. The selection and application of the appropriate sequencing, timing, and types of vibrational forces is within the ordinary skill in the art. Generally, these forces contribute to fully filling each cavity 10, so that there are not undesired voids in the finished blocks, and also to densifying the dry cast concrete so that the finished blocks will have the desired weight, density, and performance characteristics.

After densification, the pre-cured blocks are discharged from the cavities. Preferably, discharge occurs by lowering the pallet 28 relative to the mold 6, while further lowering the stripper shoes 16 through the mold cavities to assist in stripping the pre-cured blocks from the cavities. The stripper shoes are then raised upwardly out of the mold cavities and the mold is ready to repeat this production cycle.

Once the pre-cured blocks have been completely removed from the cavities, they can be transported away from the mold assembly for subsequent curing. The blocks may be cured through any means known to those of skill in the art. Examples of curing processes that are suitable for practicing the invention include air curing, autoclaving, and steam curing. Any of these processes for curing the blocks may be implemented by those of skill in the art.

Once cured, the blocks can be packaged for storage and subsequent shipment to a jobsite, and can then be used with other cured blocks in forming a structure, such as a retaining wall.

To aid in determining whether the expected densification of the concrete has occurred, certain ones of the three-dimensional patterns on the stripper shoes 16 are configured to create measurement locations on the resulting front faces of the respective blocks. The measurement locations are designed to provide reference points that are at a predetermined target distance, for example about 6 inches, away from the rear face of the respective block when adequate densification has occurred. The target distance for any particular measurement location is determined based on the desired geometry of the block. To determine whether unexpected densification has occurred, the distance between the measurement locations and the rear face is measured and compared against the target distance. If the measured distance differs from the target distance, that provides an indication that unexpected densification, either greater or less than expected, has occurred, thereby indicating that the resulting blocks may not have the desired weight, density, geometry, and performance characteristics. Comparison of the measured distance to the target distance may also provide an indication that the mold cavity was not filled with the appropriate amount of concrete.

The measurement locations can comprise any small flat area that can be replicated on the front faces of the selected blocks. For example, the measurement locations can comprise flat spots that are created on the front faces of the selected blocks by corresponding flat spots provided on the three-dimensional pattern on the stripper shoes. The measurement locations may comprise any shape, such as circular, square, oval, or rectangular, or may be irregular in shape. The measurement locations need only be large enough to enable measurement of the distance from the measurement locations to the rear face by an operator of the mold. The measurement locations are preferably kept small to minimize the visual obtrusiveness of the measurement location on the block face. However, the measurement locations should not be too small, because measurement locations that are too small may prevent accurate use of a measurement instrument, may cause the operator to have a difficult time locating the measurement locations, and small amounts of residual concrete stuck to the stripper shoe may cause the measurement location to be unusable. Preferably, the measurement locations are generally rectangular and at least about ½ inch long and ⅛ inch wide. Further, the position of the measurements locations on the front face is chosen so as to be unobtrusive on the resulting block face and to facilitate measurement of the distance. For example, the measurement locations can be on the front face adjacent either the top or bottom face of the blocks.

Figure 5:
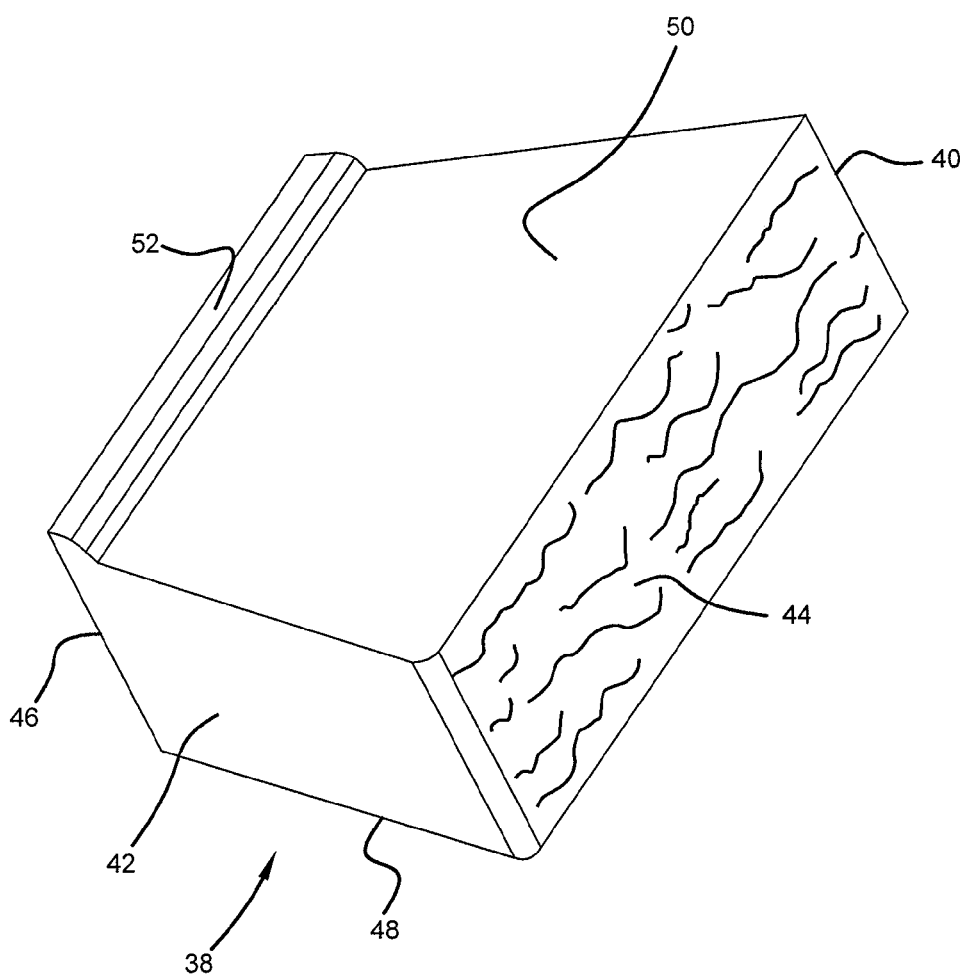
FIG. 5 is a perspective view of a block formed in one of the block-forming cavities.

FIG. 5 illustrates a block 38 formed in a cavity 10 of the mold 6, 20 without measurement locations. Block 38 comprises a pair of converging side faces 40, 42; a front face 44, a rear face 46, a top face 48, and a bottom face 50. Reference to "top" and "bottom" refers to the orientation of the surfaces during the intended use of the block. The block 38 also includes a flange 52 that extends below the bottom face 50 of the block 38 adjacent the rear face 46 and is designed to abut against the rear face of a block in the course below the block 38 to provide a pre-determined set-back from the course below and provide course-to-course shear strength. The front face 44 is an exposed, visible surface in a wall constructed from a plurality of the blocks and has the three-dimensional pattern imparted to it by the stripper shoe to enhance the appearance of the wall.

Figure 6:
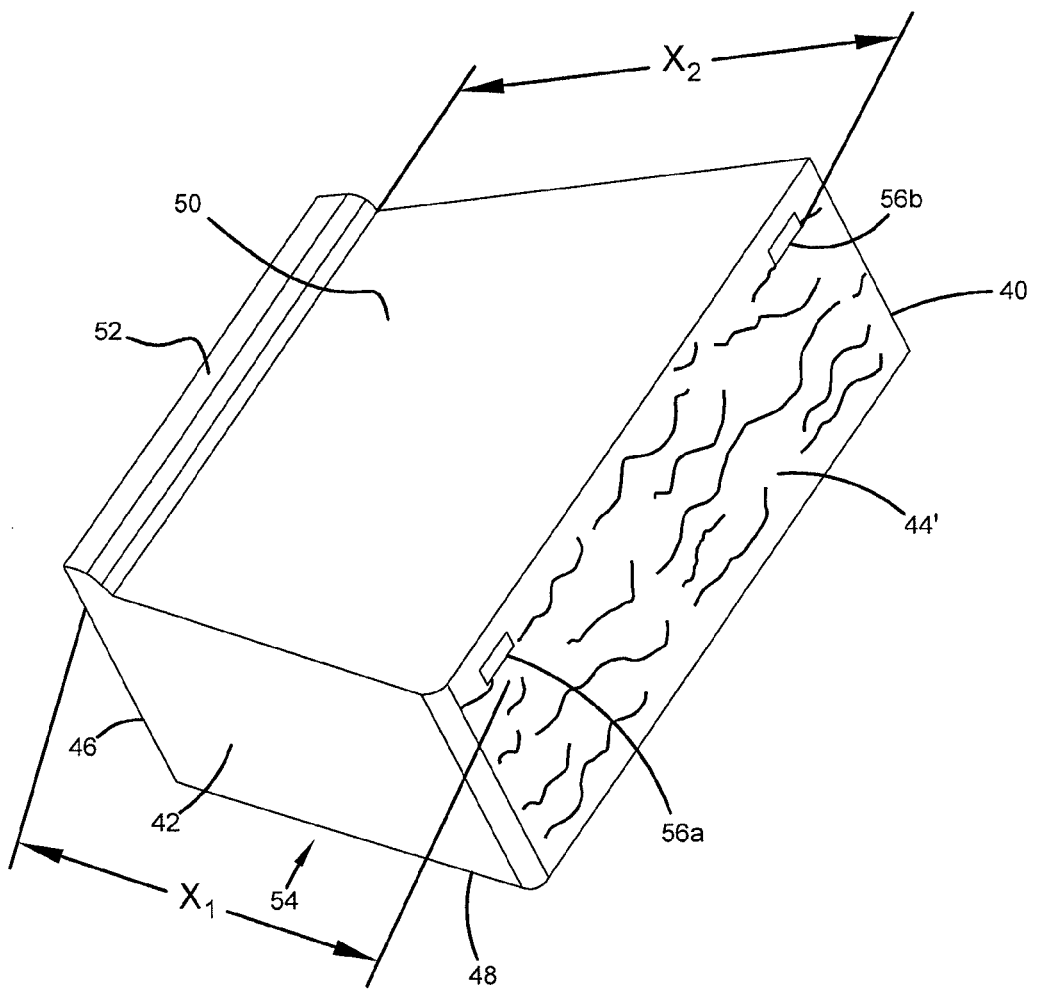
FIG. 6 is a perspective view of block formed with measurement locations in one of the predetermined block-forming cavities.
Figure 7:
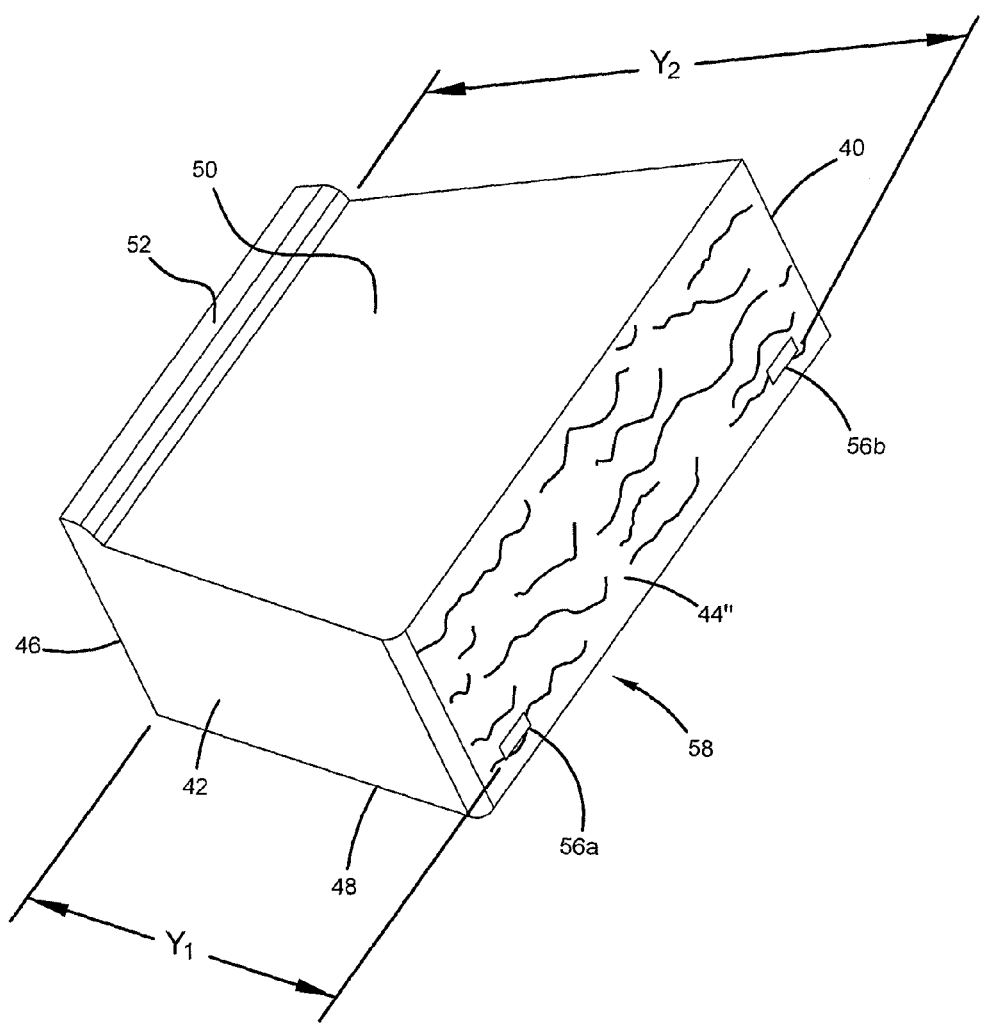
FIG. 7 is a perspective view of block with an alternative arrangement of measurement locations.

FIG. 6 illustrates a block 54 that is similar to the block 38 but is formed with measurement locations 56a, 56b. Features in the block 54 that are identical to features in the block 38 will be designated with the same reference numeral. One of the measurement locations 56a is located on the front face 44' near the corner defined by the side face 42 and the bottom face 50. The other measurement location 56b is located on the front face 44' near the corner defined by the side face 40 and the bottom face 50. Other positions for the measurement locations are possible. For example, FIG. 7 illustrates a block 58 with measurement locations 56a', 56b' formed near the corners defined by the side face 42 and the top face 48 and by the side face 40 and the top face 48. Alternative configurations of the measurement locations are possible.

The measurement locations can be formed on every block in every mold cavity 10. However, it is preferred to minimize the total number of measurement locations so as to reduce the potential visual impact of the measurement locations on the appearance of a wall or other structure constructed from the blocks. Because variability in the production of blocks may result from the pressure plates and compression head being improperly oriented relative to the mold, the number of measurement locations should be sufficient to detect mis-orientation. A total of at least three measurement locations formed on the blocks formed within mold 6, 20 will allow the plane formed by the contact of the pressure plate with the concrete in the mold cavities to be determined. These measurement locations may be formed on any block or combination of blocks within mold 6, 20.

Preferably, with reference to FIG. 8, the measurement locations are formed only on the front faces of the blocks associated with end cavities 10A and 10B, and with reference to FIG. 9, the measurement locations are most preferably formed only on the front faces of the blocks associated with the corner cavities 10C, 10D, 10E, and 10F. FIGS. 8 and 9 show the blocks formed within molds 6, 20 prior to the blocks being removed from the molds 6, 20. For clarity, FIGS. 8 and 9 show only the measurement locations on the block face and not any other features formed on the block face. Even more preferably, with reference to FIG. 8, one measurement location is formed on the block associated with cavity 10A near the corner defined by side wall 22 and end wall 24, one measurement location is formed on the block associated with cavity 10A near the corner defined by side wall 22' and end wall 24, one measurement location is formed on the block associated with cavity 10B near the corner defined by side wall 22 and end wall 24', and one measurement location is formed on the block associated with cavity 10B near the corner defined by side wall 22' and end wall 24'. This arrangement provides the further advantage of positioning the measurement locations where they are readily accessible to the mold operator. With reference to FIG. 9, even more preferably, one measurement location is formed on the block associated with cavity 10C near the corner defined by side wall 22 and end wall 24, one measurement location is formed on the block associated with cavity 10D near the corner defined by side wall 22' and end wall 24, one measurement location is formed on the block associated with cavity 10E near the corner defined by side wall 22 and end wall 24', and one measurement location is formed on the block associated with cavity 10F near the corner defined by side wall 22' and end wall 24'. This arrangement also provides the advantage of positioning the measurement locations where they are readily accessible to the mold operator.

Figure 10:
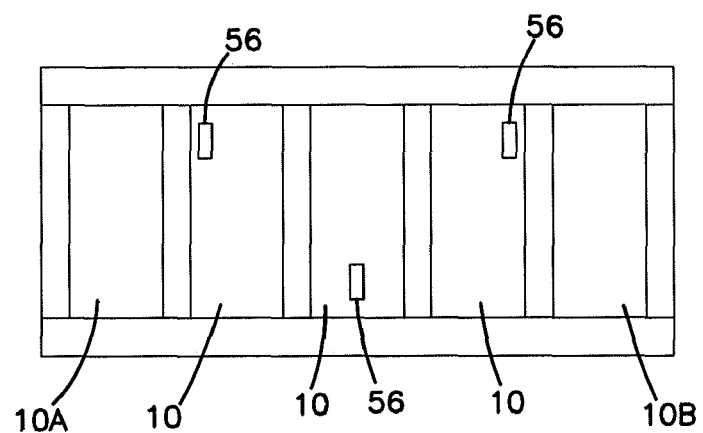
FIG. 10 is a top view of the concrete blocks formed in the mold of FIG. 2 with an alternative arrangement of measurement locations.

Alternatively, FIG. 10 shows one possible alternative arrangement of measurement locations 56 relative to the arrangement of blocks in a mold cavity 6, where a single measurement location 56 is located on the block located adjacent to the block formed in mold cavity 10A and one measurement location 56 is located on the block located adjacent to the block formed in mold cavity 10B. An additional measurement location is located on the block formed in the middle cavity of the mold. However, many other combinations of locations of the measurement locations 56 are possible.

Once a block has been removed from the mold, the straight-line distance between each measurement location and the rear face of the block can be measured. The measured straight line distances may be compared with a target straight line distance. If the measured straight line distances do not equal the target straight line distances, one knows that uneven densification has occurred across the front face of the block or that the mold cavity was not filled with the appropriate amount of concrete. This could indicate that the pressure plates were not oriented properly relative to the mold when they compacted the concrete.

For example, referring to FIG. 6, the straight-line distance $X_1$ on the block 54 from the measurement location 56a to the rear face 46 and the straight-line distance $X_2$ on the block 54 from the measurement location 56b to the rear face 46 are measured. Similarly, the straight-line distances $Y_1$ and $Y_2$ for the block 58 in FIG. 7 can be measured. In the disclosed embodiment, the front faces 44, 44', 44' are inclined rearwardly from the bottom edge to the top edge at a slight angle, for example, 10 degrees. As a result, the target values of $X_1$ and $X_2$ will generally be greater than $Y_1$ and $Y_2$.

If the block has been properly formed, $X_1$, $X_2$, $Y_1$, and $Y_2$ will each equal their respective target distances. On the other hand, if the measured distances $X_1$, $X_2$, $Y_1$, and $Y_2$ do not substantially equal the target distances, the person conducting the measurement knows that the expected densification did not take place. Further, if distance $X_1$ does not equal the target distance (or if $X_2$, $Y_1$, or $Y_2$ do not equal their target distances), one knows that uneven densification has occurred across the front face of the block. This could indicate that the stripper shoe was not level when it compacted the concrete.

Figure 2:
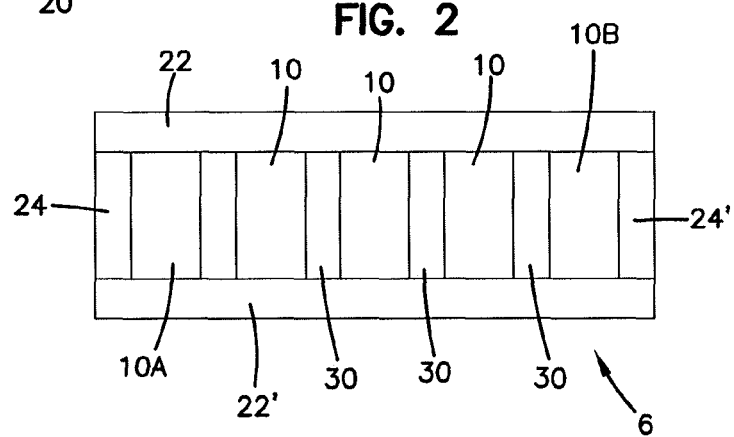
FIG. 2 is a top view of the row of block-forming cavities from the mold of FIG. 1.

Furthermore, with respect to FIG. 2, for any given production cycle, the distance measurements taken from the block formed in the cavity 10A can be compared with the distance measurements taken from the block formed in the cavity 10B. If the compression head and stripper shoes have been properly configured, the distance measurements for the block from cavity 10A and the block from cavity 10B will each equal the target distance. If there is a discrepancy in the measured distances and the target distances, that may be an indication that the compression head and/or stripper shoes are not level from one end of the mold to the other and need to be adjusted, or that the compression head and/or stripper shoes are not level from one side of the mold to the other side and need to be adjusted.

Similarly, with respect to FIG. 3, for any given production cycle, the distance measurements on the blocks from the cavities 10C, 10D, 10E and 10F can be taken and compared against the target distance to determine whether the compression head and/or stripper shoes are not level from one end of the mold to the other end and/or not level from one side to the other side of the mold. With respect to FIG. 3, the blocks in the cavities 10C, 10D, 10E and 10F could be formed with a single measurement location, rather than a pair of measurement locations. With a single measurement location on the blocks, one would still be able to determine whether the compression head and/or stripper shoes is level from one end of the mold to the other end and/or level from one side to the other side of the mold.

Similarly, the measurements of one set of blocks from one production cycle can be compared with the corresponding measurements of one set of blocks from a different production cycle to determine whether the blocks are being formed consistently from one production cycle to the next.

The invention claimed is:

1. A process for producing a plurality of concrete blocks; the process comprising the steps of:
    providing a mold having at least a first row of block-forming cavities;
        each block-forming cavity in the first row having an open top and an open bottom; the first row comprising at least five block-forming cavities comprising at least: a first end cavity; and, a second, opposite, end cavity, separated from the first end cavity by a plurality of cavities;
    positioning a single pallet under the entire first row of block forming cavities to temporarily close the open bottoms of the block-forming cavities in the first row;
    introducing dry cast concrete into each block-forming cavity in the first row, through the open top of each cavity;
    actuating a single compression head to lower a stripper shoe into each of the block-forming cavities in the first row;
        the step of actuating including compacting the dry cast concrete in each block-forming cavity to mold a pre-cured concrete block therein; each pre-cured block having a front face, a rear face and opposite side faces;
        the rear face of each pre-cured concrete block resting on the pallet during molding of the pre-cured block and conforming to the surface of the pallet during molding;
        the front face of each pre-cured block being formed facing upwardly and being molded by an associated stripper shoe to have a three-dimensional pattern that is not parallel to the rear face of the block;
        the front face of a pre-cured concrete block molded in the first end cavity having a first plurality of measurement locations thereon comprising a first plurality of flat spots molded by an associated stripper shoe; each one of the first plurality of flat spots having a minimum dimension of at least ⅛ inch and being substantially smaller in area than the front face; each flat spot in the first plurality of measurement locations corresponding to a measurement location being bordered, at least partially, by a non-flat portion of the three-dimensional pattern on the front face of the corresponding block;

the front face of a pre-cured concrete block molded in the second end cavity having a second plurality of measurement locations thereon comprising a second plurality of flat spots molded by an associated stripper shoe; each one of the second plurality of flat spots having a minimum dimension of at least ⅛ inch and being substantially smaller in area than the front face; each flat spot corresponding to a measurement location being bordered, at least partially, by a non-flat portion of the three-dimensional pattern on the front face of the corresponding block;

discharging pre-cured concrete blocks from the bottoms of the first row of block-forming cavities and onto the pallet;

measuring at least:
  the respective distances between at least two selected ones of the measurement locations on the front face of the first end block and the rear face of the first end block; and,
  the respective distances between at least two selected ones of the measurement locations on the front face of the second end block and the rear face of the second end block;

evaluating the measurements to assess molding quality, without conducting measurements on molded blocks from every one of the cavities in the first row; the step of evaluating including comparing the measurements to target distances; and, adjusting the alignment of at least one of the compression head and the stripper shoe with the mold based on results obtained from the evaluating step, if necessary.

2. The process of claim 1, wherein:
the block molded in the first end cavity has opposite top and bottom faces in use;
the block molded the second cavity has opposite top and bottom faces in use; and,
the measurement locations on the front face of the pre-cured concrete block molded in the first cavity are formed on the front face adjacent the bottom face of the block, and the measurement locations on the front face of the pre-cured concrete block formed in the second cavity are formed on the front face adjacent the top face in use of the block.

3. The process of claim 2 wherein:
the measurement locations on the front face of the pre-cured concrete block molded in the first cavity are further from the rear face of the pre-cured concrete block molded in the first cavity than the measurement locations on the first face of the pre-cured concrete block molded in the second cavity are from the rear face of the pre-cured concrete block molded in the second cavity.

4. The process of claim 1 wherein:
each pre-cured concrete block formed in the mold has a bottom face with a flange for defining set-back, in use.

5. The process of claim 1, wherein the step of providing a mold comprises providing a mold having at least two rows of block-forming cavities, each of the rows having a first end block-forming cavity at one end of the respective row and a second end block-forming cavity at an opposite end of the respective row, and the compacting includes creating a plurality of measurement locations on the front faces of the pre-cured concrete blocks formed in each of the first and second end cavities of each row.

6. The process of claim 3, wherein for each of the pre-cured blocks formed in the first and second end cavities, one of the measurement locations is formed on the front face adjacent one side face in use of the resulting block and one of the measurements locations is formed on the front face adjacent the opposite side face of the resulting block.

7. The process of claim 5 wherein:
the step of measuring includes measuring:
  the respective distances between at least two selected ones of the measurement locations on the front face of first end block in the second row and the rear face of the first end block in the second row; and,
  the respective distances between at least two selected ones of the measurement locations on the front face of the second end block in the second row and the rear face of the second end block in the second row; and,
wherein the step of evaluating comprises comparing the measurements taken on blocks formed in the first and second end cavities of the first row to target distances and comparing the measurements taken on blocks formed in the first and second end cavities of the second row to target distances.

8. The process of claim 1, wherein the step of creating measurement locations on the concrete blocks comprises creating measurement locations that are generally rectangular.

9. The process of claim 8, wherein the rectangular measurement locations are approximately ½ inch by ⅛ inch.

10. The process of claim 1, wherein each of the measurement locations has a minimum dimension of at least ½ inch by ⅛ inch.

11. The process of claim 1, wherein each of the measurement locations has a shape selected from rectangular, square, oval, and circular.

* * * * *